United States Patent
Walling et al.

(10) Patent No.: US 7,347,989 B2
(45) Date of Patent: Mar. 25, 2008

(54) HIGH EFFICACY ANTIPERSPIRANT STICK CONTAINING LOW LEVELS OF NON-VOLATILE ORGANIC

(75) Inventors: David William Walling, Cincinnati, OH (US); Phi Van Chu, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 833 days.

(21) Appl. No.: 10/797,735

(22) Filed: Mar. 10, 2004

(65) Prior Publication Data

US 2004/0197281 A1    Oct. 7, 2004

Related U.S. Application Data

(60) Provisional application No. 60/459,307, filed on Apr. 1, 2003.

(51) Int. Cl.
- *A61Q 15/00* (2006.01)
- *A61Q 19/00* (2006.01)
- *A61K 8/02* (2006.01)
- *A61K 8/06* (2006.01)

(52) U.S. Cl. .......................... 424/65; 424/68; 424/400; 424/401

(58) Field of Classification Search .................. 424/65, 424/68, 400, 401
See application file for complete search history.

(56) References Cited

U.S. PATENT DOCUMENTS

| | | | |
|---|---|---|---|
| 4,174,386 A | 11/1979 | Spitzer et al. | |
| 4,183,911 A | 1/1980 | Smithies et al. | |
| 5,942,215 A | 8/1999 | Edwards et al. | |
| 6,221,345 B1 * | 4/2001 | Esser | 424/65 |
| 6,352,688 B1 | 3/2002 | Scavone et al. | |
| 6,361,765 B1 | 3/2002 | Emslie et al. | |
| 6,383,476 B1 | 5/2002 | Scavone et al. | |
| 6,406,684 B1 | 6/2002 | Fecht et al. | |
| 6,451,295 B1 | 9/2002 | Cai et al. | |

FOREIGN PATENT DOCUMENTS

EP    0117070    8/1984

OTHER PUBLICATIONS

Ernest W. Flick, "Cosmetic and Toiletry Formulations" Online!, 1999, ISBN: 0-8155-1430-1, William Andrew Publishing/Noyes, Norwich, New York, USA.

Personal Care Polymers, Online!, May 15, 2001, XP002297277, "Silky Smooth Antiperspirant Stick" 7528-127A, URL:http//www.personalcarepolymers.com/doc/en/formulation/7528127A.pdf.

Chang I B et al., "Antiperspirant Sticks Modified with Low Molecular Weight Polyethylenes and Ethylene Copolymers", Nov. 1989, pp. 115-124, vol. 11 No 104, Cosmetics and Toiletries, Wheaton, IL, USA.

* cited by examiner

*Primary Examiner*—Shelley A. Dodson
(74) *Attorney, Agent, or Firm*—Vladimir Vitenberg; Andrew L. Hagerty; Brian M. Bolam

(57) ABSTRACT

An antiperspirant stick product comprising from about 5% to about 35% by weight of an antiperspirant active; from about 5% to about 35% by weight of a structurant, from about 20% to about 80% by weight of a volatile fluid; 10% or less by weight of a non-volatile organic fluid; free of non-volatile silicone fluids, wherein the stick has a hardness of at least about 600 gram·force and an adhesion value of at least 33%.

20 Claims, No Drawings

HIGH EFFICACY ANTIPERSPIRANT STICK CONTAINING LOW LEVELS OF NON-VOLATILE ORGANIC

CROSS REFERENCE TO RELATED APPLICATION

This application claims the benefit under 35 USC 119(e) to U.S. application Ser. No. 60/459,307, filed Apr. 1, 2003.

FIELD OF THE INVENTION

The present invention relates to antiperspirant stick compositions for application to human skin, especially the axilla. More particularly, the present invention relates to high adhesion and high antiperspirant efficacy compositions containing relatively low levels of non-volatile organic fluids.

BACKGROUND OF THE INVENTION

There are many types of solid antiperspirant sticks that are commercially available or otherwise known in the antiperspirant art. These products typically contain an astringent material, e.g. zirconium or aluminum salts or combinations thereof, solubilized or dispersed in a suitable liquid carrier, and the solution or dispersion contained within a solid matrix that gives the product a solid stick form.

These solid antiperspirant sticks are ideally designed to provide effective perspiration and odor control while also being cosmetically acceptable during and after application onto the underarm area of the skin. In this context, "cosmetically acceptable" means that the product glides on smoothly during application, is non-irritating, and results in little or no visible residue (e.g., low residue performance) after application to the skin.

It is well known in the art that once applied to the underarm area, an antiperspirant film must have a certain level of adhesion to the skin in order to be effective. It is further known that using non-volatile liquids are one way to promote good adhesive properties in antiperspirant products. See, for example, U.S. Pat. Nos. 4,183,911; 4,174,386; 6,406,684; 6,451,295; 6,352,688; and 6,383,476. It is also known in the art that high levels of non-volatile organic fluids inhibit antiperspirant efficacy by impeding release characteristics from the applied product matrix. See, for example, U.S. Pat. Nos. 6,352,688; 6,383,476. Not wishing to be limited by theory, we believe that the non-volatile liquids promote adhesion by plasticizing the dried film applied to the skin.

Thus, prior art suggests that the higher the level of non-volatile liquids the better adhesion of the antiperspirant film to the skin can be achieved. At the same time, it is known in the art that high levels of non-volatile organic components negatively affect the product efficacy.

SUMMARY OF THE INVENTION

Therefore, it was surprising to discover that by formulating a solid antiperspirant stick having a relatively low, in comparison to the teachings of prior art, content of a non-volatile organic liquids can have both a good adhesion and an excellent antiperspirant efficacy. More specifically, the present invention is directed to a solid antiperspirant stick comprising from about 5% to about 35% by weight of an antiperspirant active; from about 5% to about 35% by weight of a structurant; from about 20% to about 80% by weight of a volatile fluid; and 10% or less by weight of a non-volatile organic fluid; wherein the stick has a hardness of at least about 600 gram·force and an adhesion value of at least 33%, and more specifically at least 40%, as can be tested by the method described herein, and wherein the stick has no non-volatile silicone fluids.

The active can be selected from the group consisting of aluminum-containing salts and zirconium-containing salts or materials, such as, for example, aluminum halides, aluminum hydroxyhalides, zirconyl oxyhalides, zirconyl hydroxyhalides, and mixtures thereof.

The structurant can be selected from the group consisting of stearyl alcohol and other fatty alcohols; hydrogenated castor oil; paraffin wax; beeswax; carnauba; candelilla; spermeceti wax; ozokerite; ceresin; baysberry; synthetic waxes, such as Fisher-Tropsch waxes and microcrystalline wax; polyethylenes with molecular weight of about 200 to about 1000 daltons; solid triglycerides; and any mixtures thereof.

The volatile fluid can be selected from the group consisting of cyclic, linear and/or branched chain silicones having the requisite volatility as defined herein, and mixtures thereof.

The non-volatile fluid can be selected from the group consisting of mineral oil; PPG-14 butyl ether; isopropyl myristate; petrolatum; butyl stearate; cetyl octanoate; butyl myristate; myristyl myristate; C12-15 alkylbenzoate (e.g., Finsolv.™.); octyldodecanol; isostearyl isostearate; octododecyl benzoate; isostearyl lactate; isostearyl palmitate; isobutyl stearate; and any mixtures thereof.

The product of the present invention can further comprise a fragrance and/or at least one of the group consisting of vitamins, medications, dyes or colorants; emulsifiers; perfumes; distributing agents; antimicrobials; deodorant perfumes; pharmaceutical or other topical actives; preservatives; surfactants; etc., and mixtures thereof.

The product can further comprise film modifiers selected from the group consisting of powders, silica, flow beads, and mixtures thereof.

DETAILED DESCRIPTION OF THE INVENTION

The anhydrous, low-residue, antiperspirant stick compositions of the present invention comprise as essential ingredients particulate antiperspirant active, suspending agent, volatile silicone, and non-volatile organic liquids. Each is described in detail hereinafter.

The term "anhydrous" as used herein means that the antiperspirant stick composition of the present invention, and the essential or optional components thereof, are substantially free of added or free water. From a formulation standpoint, this means that the anhydrous antiperspirant stick compositions of the present invention contain less than about 1%, and more specifically zero percent, by weight of free or added water, other than the water of hydration typically associated with the particulate antiperspirant active prior to formulation.

All melt points referenced herein, unless otherwise specified, are measured by well known technique of Differential Scanning Calorimetry (DSC). An example of this technique is described in U.S. Pat. No. 5,306,514, issued on Apr. 26, 1994 to Letton et al., which description is incorporated herein by reference.

The term "ambient conditions" as used herein refers to surrounding conditions under about one atmosphere of pressure, at about 50% relative humidity, and at about 25° C., unless otherwise specified. All values, amounts, and measurements described herein are obtained under ambient conditions unless otherwise specified.

The term "volatile" as used herein refers to those materials that have a measurable vapor pressure at 25° C. Such vapor pressures typically range from about 0.01 millimeters of Mercury (mm Hg) to about 6 mmHg, more typically from about 0.02 mmHg to about 1.5 mmHg; and have an average boiling point at one (1) atmosphere of pressure of less than about 250° C., more typically less than about 235° C. Conversely, the term "non-volatile" refers to those materials that are not "volatile" as defined herein.

The term "skin temperature" as used herein refers to the temperature of the axilla area of the skin, which is generally at or slightly below a typical body temperature of about 37° C.

The anhydrous antiperspirant stick compositions of the present invention can comprise, consist of, or consist essentially of the essential elements and limitations of the invention described herein, as well as any additional or optional ingredients, components, or limitations known or otherwise effective for use in such compositions.

All percentages, parts and ratios are by weight of the total composition, unless otherwise specified. All such weights as they pertain to the listed ingredients are based on the specific ingredient level and, therefore, do not include solvents, carriers, by-products, filler or other minor ingredients that may be included in commercially available materials, unless otherwise specified.

Hardness

The anhydrous antiperspirant stick compositions of the present invention have a product hardness of least about 600 gram·force, more specifically from about 600 gram·force to about 5,000 gram·force, still more specifically from about 750 gram·force to about 2,000 gram·force, and yet more specifically from about 800 gram·force to about 1,400 gram·force.

The term "product hardness" or "hardness" as used herein is a reflection of how much force is required to move a penetration cone a specified distance and at a controlled rate into an antiperspirant stick composition under the test conditions described herein below Higher values represent harder product, and lower values represent softer product. These values are measured at 27° C., 15% relative humidity, using a TA-XT2 Texture Analyzer, available from Texture Technology Corp., Scarsdale, N.Y., U.S.A. The product hardness value as used herein represents the peak force required to move a standard 45-degree angle penetration cone through the composition for a distance of 10 mm at a speed of 2 mm/second. The standard cone is available from Texture Technology Corp., as part number TA-15, and has a total cone length of about 24.7 mm, angled cone length of about 18.3 mm, and a maximum diameter of the angled surface of the cone of about 15.5 mm. The cone is a smooth, stainless steel construction and weighs about 17.8 grams.

Adhesion

The anhydrous antiperspirant stick compositions of the present invention have a dried film adhesion value of at least about 33% and more specifically at least about 40%. The term "dried film adhesion value" as used herein is a reflection of adhesive properties of dried antiperspirant films by the method described immediately below.

Polyurethane film U073 from Deerfield Urethane, having surface energy of 55.62 mJ/m², can be used as the test substrate. First, strips of the polyurethane having dimensions of 76.2 mm×31.8 mm are cut. Using a black marker, a 50.8 mm×28.6 mm rectangle is drawn in the center of a non-shiny side of the 76.2 mm×31.8 mm polyurethane strip. Then, the shiny backing is removed by applying scotch tape to the backing and peeling the polyurethane away from the backing. The polyurethane strip is weighed (wt. A) to the nearest 0.1 mg and then carefully placed fresh (the side from which the shiny backing is removed) side up. Care must be taken to not touch inside the marked rectangle with bare fingers throughout the remainder of the test. Then the tested product, in the amount of 0.0375±0.0010 mg, is applied to the fresh side of the film. The product is spread in a thin, uniform coating across the entire 50.8 mm×28.6 mm rectangle using a metal spatula or similar device. The sample is carefully placed into an oven at 38° C. for 24 hours, after which time the sample is removed from the oven and reweighed (wt. B). The sample is then placed into a Texture Analyser (model TA-XT2i from Texture Technologies Corp.). Compression grips (TA-96 Tensile Test Fixture) can be used to firmly hold the sample vertically in place. To load the test polyurethane strip, the grips are positioned at a distance of 50.8 mm apart from one another and the coated rectangular portion of the strip is centered between the grips. Once securely loaded, the strip is pulled at a speed of 10 mm/sec to a strain of 175% (corresponding 88.9 mm).

Then the sample is carefully removed from the grips and is fastened to a plastic cup, or equivalent thereof, using a standard paper clip or its equivalent. The cup is then shaken on Vortex shaker (Fisher Scientific—Fisherbrand$^R$ Vortex Genie 2™ 12-812) at a "6" gage speed for 20 seconds. After shaking is complete, the sample is reweighed (wt. C). The percent adhesion is then calculated using the formula:

% Adhesion=[(wt. C−wt. A)/(wt. B−wt. A)]·100.

Samples are run in triplicate with the average of the three readings used as the final Adhesion Value for a test product.

Essential Ingredients

Structurants

The anhydrous antiperspirant stick compositions of the present invention comprise a suitable concentration of a solid structurant to help provide the compositions with the desired viscosity, rheology, texture and/or product hardness, or to otherwise help suspend any dispersed solids or liquids within the composition.

The term "solid structurant" as used herein means any material known or otherwise effective in providing suspending, gelling, viscosifying, solidifying and/or thickening properties to the composition or which otherwise provide structure to the final product form. These solid structurants include gelling agents, and polymeric or non-polymeric or inorganic thickening or viscosifying agents. Such materials will typically be solids under ambient conditions and include organic solids, crystalline or other gellants, inorganic particulates such as clays or silicas, or combinations thereof.

The concentration and type of solid structurant selected for use in the antiperspirant compositions will vary depending upon the desired product hardness, rheology, and/or other related product characteristics. For most structurants suitable for use herein, the total structurant concentration ranges from about 5% to about 35%, more typically from about 10% to about 30% by weight of the composition.

Non-limiting examples of suitable suspending agents include stearyl alcohol and other fatty alcohols; hydrogenated castor oil (e.g., Castorwax MP80, Castor Wax, etc.); hydrocarbon waxes include paraffin wax, beeswax, carnauba, candelilla, spermeceti wax, ozokerite, ceresin, baysberry, synthetic waxes such as Fisher-Tropsch waxes, and microcrystalline wax; polyethylenes with molecular weight of 200 to 1000 daltons; and solid triglycerides; and combinations thereof, at concentrations ranging from about 5% to about 35%, preferably from about 10% to about 25 by weight of the product.

Other non-limiting examples of suspending agents suitable for use herein are described in U.S. Pat. No. 5,976,514 (Guskey et al.) and U.S. Pat. No. 5,891,424 (Bretzler et al.), which descriptions are incorporated herein by reference.

Antiperspirant Active

The anhydrous antiperspirant stick compositions of the present invention comprise a particulate antiperspirant active suitable for application to human skin. The concentration of antiperspirant active in the composition should be sufficient to provide the desired perspiration wetness and odor control from the antiperspirant stick formulation selected.

The anhydrous antiperspirant stick compositions of the present invention comprise an antiperspirant active at concentrations of from about 0.5% to about 60%, and more specifically from about 5% to about 35%, by weight of the composition. These weight percentages are calculated on an anhydrous metal salt basis exclusive of water and any complexing agents such as, for example, glycine, and glycine salts. The antiperspirant active as formulated in the composition are in the form of dispersed particulate solids having a preferred average particle size or equivalent diameter of less than about 100 microns, more specifically less than about 20 microns, and even more specifically less than about 10 microns.

The antiperspirant active for use in the anhydrous antiperspirant compositions of the present invention may include any compound, composition or other material having antiperspirant activity. More specifically, the antiperspirant actives may include astringent metallic salts, especially inorganic and organic salts of aluminum, zirconium and zinc, as well as mixtures thereof. Even more specifically, the antiperspirant actives may include aluminum-containing and/or zirconium-containing salts or materials, such as, for example, aluminum halides, aluminum chlorohydrate, aluminum hydroxyhalides, zirconyl oxyhalides, zirconyl hydroxyhalides, and mixtures thereof.

Aluminum salts for use in the anhydrous antiperspirant stick compositions include those that conform to the formula:

$$Al_2(OH)_aCl_b \cdot xH_2O,$$

wherein a is from about 2 to about 5;

the sum of a and b is about 6;

x is from about 1 to about 6; and a, b, and x may have non-integer values.

More specifically, aluminum chlorohydroxides referred to as "5/6 basic chlorohydroxide" may be used, wherein a=5, and "2/3 basic chlorohydroxide", wherein a=4.

Processes for preparing aluminum salts are disclosed in U.S. Pat. No. 3,887,692, Gilman, issued Jun. 3, 1975; U.S. Pat. No. 3,904,741, Jones et al., issued Sep. 9, 1975; U.S. Pat. No. 4,359,456, Gosling et al., issued Nov. 16, 1982; and British Patent Specification 2,048,229, Fitzgerald et al., published Dec. 10, 1980, the disclosures of which are incorporated herein by reference for the purpose of describing processes for preparing aluminum salts.

Mixtures of aluminum salts are described in British Patent Specification 1,347,950, Shin et al., published Feb. 27, 1974, which description is also incorporated herein by reference.

Preferred zirconium salts for use in the anhydrous antiperspirant stick compositions include those which conform to the formula:

$$ZrO(OH)_{2-a}Cl_a \cdot xH_2O,$$

wherein a is from about 1.5 to about 1.87;

x is from about 1 to about 7; and a and x may both have non-integer values.

These zirconium salts are described in Belgian Patent 825,146, Schmitz, issued Aug. 4, 1975, which description is incorporated herein by reference. Zirconium salts that additionally contain aluminum and glycine, commonly known as "ZAG complexes," are believed to be especially beneficial. These ZAG complexes contain aluminum chlorohydroxide and zirconyl hydroxy chloride conforming to the above-described formulas. Such ZAG complexes are described in U.S. Pat. No. 3,679,068, Luedders et al., issued Feb. 12, 1974; Great Britain Patent Application 2,144,992, Callaghan et al., published Mar. 20, 1985; and U.S. Pat. No. 4,120,948, Shelton, issued Oct. 17, 1978, disclosures of which are incorporated herein by reference for the limited purpose of describing ZAG complexes.

Volatile Fluid

The antiperspirant composition of the present invention comprises a volatile silicone solvent at concentrations ranging from about 20% to about 80%, and more specifically from about 30% to about 70%, by weight of the composition. The volatile silicone of the solvent may be cyclic or linear.

"Volatile silicone" as used herein refers to those silicone materials that have measurable vapor pressure under ambient conditions. Non-limiting examples of suitable volatile silicones are described in Todd et al., "Volatile Silicone Fluids for Cosmetics", Cosmetics and Toiletries, 91:27-32 (1976), which descriptions are incorporated herein by reference.

The volatile silicone is preferably a cyclic silicone having from 3 to 7, and more specifically from 5 to 6, silicon atoms, and still more specifically 5. These cyclic silicone materials will generally have viscosities of less than about 10 centistokes at 25° C.

Linear volatile silicone materials suitable for use in the antiperspirant compositions include those represented by the formula:

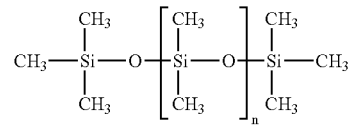

wherein n is from 1 to 7, and more specifically from 2 to 3. These linear silicone materials will generally have viscosities of less than about 5 centistokes at 25° C.

Specific examples of volatile silicone solvents suitable for use in the antiperspirant compositions include, but are not limited to, Cyclometicone D-5; GE 7207 and GE 7158 (commercially available from General Electric Co.); Dow Corning 344; Dow Corning 345; Dow Corning 200; and DC1184 (commercially available from Dow Corning Corp.); and SWS-03314 (commercially available from SWS Silicones).

Non-Volatile Organic Fluids

Surprisingly, it has been found that the adhesion value and the antiperspirant efficacy of the solid antiperspirant sticks of the present invention can be maintained at high levels by including a nonvolatile organic fluid content of less than 10% in the final formula.

Non-limiting examples of nonvolatile organic fluids include mineral oil, PPG-14 butyl ether, isopropyl myristate, petrolatum, butyl stearate, cetyl octanoate, butyl myristate, myristyl myristate, C12-15 alkylbenzoate (e.g., Finsolv.™.), octyldodecanol, isostearyl isostearate, octododecyl benzoate, isostearyl lactate, isostearyl palmitate, and isobutyl stearate.

Optional Ingredients

The anhydrous antiperspirant compositions of the present invention may further comprise any optional material that is known for use in antiperspirant and deodorant compositions or other personal care products, or which is otherwise suitable for topical application to human skin. Nonlimiting examples of optional materials include dyes or colorants, emulsifiers, perfumes, distributing agents, antimicrobials, deodorant perfumes, pharmaceutical or other topical active, preservatives, surfactants, and so forth. Examples of such optional materials are described in U.S. Pat. No. 4,049,792 (Elsnau); U.S. Pat. No. 5,019,375 (Tanner et al.); and U.S. Pat. No. 5,429,816 (Hofrichter et al.); which descriptions are incorporated herein by reference.

Methods of Manufacture

The anhydrous antiperspirant stick compositions of the present invention may be prepared by any known or otherwise effective technique, suitable for formulating an antiperspirant stick composition having the product characteristics described herein.

For example, the antiperspirant stick compositions can be formulated by mixing the volatile silicone and nonvolatile organic fluid materials under ambient conditions, or under conditions sufficient to render the admixture fluid or liquid, and then adding any suspending agents to the mixture and heating the resulting mixture sufficiently to liquefy the added suspending agents, e.g., at approximately 85° C. for many wax solids, to form a single phase liquid. Antiperspirant solids can then be added to and dispersed throughout the heated, single-phase liquid before allowing the resulting combination to cool to approximately 78° C., at which point perfumes and similar other materials (if any) can be mixed into the combination. The combination can then be cooled to just above the solidification point of the suspending agent (e.g., typically about 60° C.), deposited into dispensing packages, and allowed to solidify under ambient conditions.

More specifically, a 100-gram batch of the product has been prepared by combining in a 250 ml container stearyl alcohol (16 gm), hydrogenated castor oil (4.75 gm), behenyl alcohol (0.2 gm), cyclopentasiloxane (49.8 gm), mineral oil (0.75 gm), petrolatum (3.5 gm), and PPG 14 butyl ether (1 gm). The ingredients are heated with agitation on an IKA RET control viscosity stir plate to 85° C., with the agitation set at 400 rpm. Once the combined ingredients reach 85° C., 24 gm of aluminum zirconium trichlorohydrex glycinate (such as, for example, Westchlor ZR 60B DM HBD Powder) are added with agitation while maintaining the temperature at 85° C. The combined ingredients are then cooled with agitation on the IKA hotplate from 85° C. to about 65° C. On reaching 65° C., the beaker is removed from the hotplate and the mixture rapidly poured into an antiperspirant stick. The stick is allowed to set-up undisturbed for about 20-30 minutes. The stick may then be stored under ambient conditions.

Non-limiting examples of other suitable manufacturing methods are described in U.S. Pat. No. 4,822,603 (Farris et al.), which description is incorporated herein by reference.

Method of Use

The anhydrous antiperspirant stick compositions of the present invention may be applied topically to the axilla or other area of the skin in an amount effective to treat or reduce perspiration wetness and malodor. The composition is preferably applied in an amount ranging from about 0.1 gram to about 20 grams, more specifically from about 0.1 gram to about 10 grams, and even more specifically from about 0.1 gram to about 1 gram, to the desired area of the skin (e.g., an axilla). The compositions are preferably applied one to two times daily, preferably once daily, to achieve effective antiperspirant and malodor control over an extended period.

EXAMPLES

The following non-limiting examples illustrate specific embodiments of the antiperspirant stick compositions of the present invention, including methods of manufacture and use.

Each of the exemplified compositions is prepared by combining all of the listed components except the antiperspirant active. The combined components are heated to about 85° C. with agitation to form a hot liquid, after which all other materials are added to the heated liquid under normal agitation conditions. The heated liquid is allowed to cool with agitation until just before the point of solidification, at which point the cooled, liquid composition is filled into applicator packages and allowed to cool further and solidify to the requisite product hardness.

Each of the exemplified compositions has a product hardness of between about 600 and about 5,000 gram·force, and a dried film adhesion of at least 33%. Each of the exemplified compositions is applied topically to the axilla area of the skin, in accordance with the methods of use described herein, and provide improved antiperspirant efficacy.

All exemplified amounts are weight percentages based upon the total weight of the antiperspirant stick composition, unless otherwise specified.

The results of tests are summarized in the following table:

| Examples | Wt % | | | | | |
| --- | --- | --- | --- | --- | --- | --- |
| Ingredient | Example 1 | Example 2 | Example 3 | Example 4 | Example 5 | Example 6 |
| Cyclopentasiloxane | 49.8 | 47.55 | 45.3 | 46.3 | 46.3 | 48.8 |
| Al-ZR trichlorohydrex glycinate (solid) | 24 | 24 | 24 | 24 | 24 | 24 |
| Stearyl Alcohol | 16 | 16 | 18 | 16 | 15 | 16 |

-continued

| Examples | Wt % | | | | | |
|---|---|---|---|---|---|---|
| Ingredient | Example 1 | Example 2 | Example 3 | Example 4 | Example 5 | Example 6 |
| Hydrogenated Castor Oil | 4.75 | 4.75 | 3 | 4.75 | 5.75 | 4.75 |
| Behenyl Alcohol | 0.2 | 0.2 | 0.2 | 0.2 | 0.2 | 0.2 |
| Silica | 0 | 0 | 0 | 0.25 | 0.25 | 0 |
| PPG-14 Butyl Ether | 1 | 4 | 5 | 5 | 5 | 2 |
| Mineral Oil | 0.75 | 0.5 | 2.5 | 2.5 | 1.5 | 2.5 |
| Petrolatum | 3.5 | 3 | 1 | 1 | 0 | 1.75 |
| PEG 8 Distearate | 0 | 0 | 1 | 0 | 0 | 0 |
| Myristyl Myristate | 0 | 0 | 0 | 0 | 2 | 0 |
| % Non-Volatile Organic Fluid | 5.25 | 7.5 | 9.5 | 8.5 | 8.5 | 6.25 |
| Hardness | 1715 | 1535 | 1250 | 1300 | 1200 | 1675 |
| Adhesion Value (%) | 33 | 37 | 38 | 41 | 34 | 34 |

The antiperspirant and deodorant embodiments of the present invention can also be formulated with deodorant active in addition to or in place of the antiperspirant active described hereinbefore. The term "deodorant active" as used herein includes antimicrobial agents (e.g. bacteriocides, fungicides), malodor-absorbing materials, perfume chemicals that deodorize or mask body odor or which otherwise provide the desired fragrance, or combinations thereof. The concentration of deodorant active can vary with the particular active selected, but typically ranges from about 0.1% to about 10%, and more specifically from about 0.1% to about 5%, by weight of the composition.

Non-limiting examples of deodorant actives comprising antimicrobial agents include cetyl-trimethylammonium bromide; cetyl pyridinium chloride; benzethonium chloride; diisobutyl phenoxy ethoxy ethyl dimethyl benzyl ammonium chloride; sodium N-lauryl sarcosine; sodium N-palmethyl sarcosine; lauroyl sarcosine; N-myristoyl glycine, potassium N-lauryl sarcosine; trimethyl ammonium chloride; sodium aluminum chlorohydroxy lactate; triethyl citrate; tricetylmethyl ammonium chloride; 2,4,4'-trichloro-2'-hydroxy diphenyl ether (triclosan); 3,4,4'-trichlorocarbanilide (triclocarban); diaminoalkyl amides such as L-lysine hexadecyl amide; heavy metal salts of citrate, salicylate, and piroctose, especially zinc salts, and acids thereof; heavy metal salts of pyrithione, especially zinc pyrithione, zinc phenolsulfate, farnesol, phenoxyethanol; and combinations thereof.

All document cited in the Detailed Description of the Invention are, in relevant part, incorporated herein by reference, the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

We claim:

1. An antiperspirant stick product comprising
   (a) from about 5% to about 35% by weight of an antiperspirant active;
   (b) from about 5% to about 35% by weight of a structurant,
   (c) from about 20% to about 80% by weight of a volatile fluid; and
   (d) 10% or less by weight of a non-volatile organic fluid;
   wherein, the stick has a hardness of at least about 600 gram·force and an adhesion value of at least 33%, and wherein the stick is free of non-volatile silicone fluids.

2. The product of claim 1, wherein the antiperspirant active is from about 10% to about 30%.

3. The product of claim 1, wherein the structurant is from about 10% to about 25%.

4. The product of claim 1, wherein the volatile fluid is from about 30% to about 70%.

5. The product of claim 1, wherein the non-volatile organic fluid is 8% or less.

6. The product of claim 1, wherein the non-volatile organic fluid is less than about 7%.

7. The product of claim 1, wherein the active is selected from the group consisting of aluminum-containing salts and zirconium-containing salts or materials.

8. The product of claim 7, wherein the active is selected from the group consisting of at least one of aluminum halides, aluminum hydroxyhalides, zirconyl oxyhalides, zirconyl hydroxyhalides, and any mixture thereof.

9. The product of claim 1, wherein the structurant is selected from the group consisting of stearyl alcohol and other fatty alcohols; hydrogenated castor oil; paraffin wax; beeswax; carnauba; candelilla; spermeceti wax; ozokerite; ceresin; baysberry; synthetic waxes, such as Fisher-Tropsch waxes and microcrystalline wax; polyethylenes with molecular weight of 200 to 1000 daltons; solid triglycerides; and any mixtures thereof.

10. The product of claim 1, wherein the volatile fluid is selected from the group consisting of cyclic silicones; linear silicones; branched chain silicones; and mixtures thereof.

11. The product of claim 1, wherein the non-volatile organic fluid is selected from the group consisting of mineral oil; PPG-14 butyl ether; isopropyl myristate; petrolatum; butyl stearate; cetyl octanoate; butyl myristate; myristyl myristate; C12-15 alkylbenzoate; octyldodecanol; isostearyl isostearate; octododecyl benzoate; isostearyl lactate; isostearyl palmitate; isobutyl stearate; and any mixtures thereof.

12. The product of claim 1, wherein the adhesion value is at least 40%.

13. The product of claim 1, wherein the product further comprises film modifiers selected from the group consisting of powders, silica, flow beads, and mixtures thereof.

14. The product of claim 1, wherein the product further comprises at least one of the group consisting of vitamins, medications, dyes, colorants, emulsifiers, perfumes, fragrances, distributing agents, antimicrobials, deodorant materials, pharmaceutical and other topical active, preservatives, surfactants, and mixtures thereof.

15. The product of claim 1, wherein the product contains less than about 1% by weight of free or added water.

16. The product of claim 1, wherein the volatile fluid comprises a volatile silicone material.

17. The product of claim 1, wherein the non-volatile organic fluid is included in an amount from about 5.25% to about 9.5% by weight.

18. The product of claim 17, wherein the non-volatile organic fluid comprises petrolatum.

19. The product of claim 17, wherein the non-volatile organic fluid comprises a combination of at least two of PPG-14 butyl ether, petrolatum, and mineral oil.

20. An antiperspirant stick product comprising
    (a) from about 5% to about 35% by weight of an antiperspirant active;
    (b) from about 10% to about 25% by weight of a structurant,
    (c) from about 30% to about 70% by weight of a volatile silicone fluid; and
    (d) from about 5.25% to about 9.5% by weight of a non-volatile organic, fluid;
    wherein the stick has a hardness of at least about 600 gram·force, an adhesion value of at least 33%, is free of non-volatile silicone fluids, and contains less than about 1% by weight of free or added water.

* * * * *